United States Patent
Wang et al.

(10) Patent No.: US 8,687,186 B2
(45) Date of Patent: Apr. 1, 2014

(54) NANOWIRE-BASED SYSTEMS FOR PERFORMING RAMAN SPECTROSCOPY

(75) Inventors: Shih-Yuan Wang, Palo Alto, CA (US); Jingjing Li, Palo Alto, CA (US); Huei Pei Kuo, Cupertino, CA (US); David A. Fattal, Mountain View, CA (US); Nobuhiko Kobayashi, Sunnyvale, CA (US); Zhiyong Li, Redwood City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 13/383,387

(22) PCT Filed: Jul. 30, 2009

(86) PCT No.: PCT/US2009/052308
§ 371 (c)(1),
(2), (4) Date: Jan. 10, 2012

(87) PCT Pub. No.: WO2011/014176
PCT Pub. Date: Feb. 3, 2011

(65) Prior Publication Data
US 2012/0113419 A1    May 10, 2012

(51) Int. Cl.
*G01J 3/44*        (2006.01)
(52) U.S. Cl.
USPC .......................................................... 356/301
(58) Field of Classification Search
USPC ............................................. 356/301, 72–73
See application file for complete search history.

(56) References Cited

U.S. PATENT DOCUMENTS

| | | | |
|---|---|---|---|
| 7,158,219 B2 | 1/2007 | Li et al. |
| 7,224,451 B2 | 5/2007 | Naya |
| 7,236,242 B2 | 6/2007 | Kamins et al. |
| 7,288,419 B2 | 10/2007 | Naya |
| 7,351,588 B2 | 4/2008 | Poponin |
| 7,388,661 B2 | 6/2008 | Li et al. |
| 7,426,025 B2 | 9/2008 | Wang |
| 7,476,787 B2 | 1/2009 | Thomas et al. |

(Continued)

FOREIGN PATENT DOCUMENTS

| | | |
|---|---|---|
| JP | 2005-524857 A | 12/2003 |
| JP | 2006-349463 A | 12/2006 |

(Continued)

OTHER PUBLICATIONS

Hewlett-Packard Development Company, International Search Report and Written Opinion of the ISA, PCT/US/2009/052308, Report dated Apr. 27, 2010.

(Continued)

*Primary Examiner* — Tarifur Chowdhury
*Assistant Examiner* — Abdullahi Nur

(57) ABSTRACT

Embodiments of the present invention are directed to nanowire-based systems for performing surface-enhanced Raman spectroscopy. In one embodiment, a system comprises a substrate having a surface and a plurality of tapered nanowires disposed on the surface. Each nanowire has a tapered end directed away from the surface. The system also includes a plurality of nanoparticles disposed near the tapered end of each nanowire. When each nanowire is illuminated with light of a pump wavelength, Raman excitation light is emitted from the tapered end of the nanowire to interact with the nanoparticles and produce enhanced Raman scattered light from molecules located in close proximity to the nanoparticles.

14 Claims, 12 Drawing Sheets

(56) References Cited

U.S. PATENT DOCUMENTS

| | | |
|---|---|---|
| 7,576,854 B2 | 8/2009 | Wang |
| 7,586,601 B2 | 9/2009 | Ebstein |
| 7,609,378 B2 | 10/2009 | Konakahara |
| 7,651,863 B2 | 1/2010 | Hulteen |
| 7,656,525 B2 | 2/2010 | Zhao |
| 7,707,647 B2 | 4/2010 | Konakahara |
| 7,965,388 B2 * | 6/2011 | Xia et al. ............. 356/301 |
| 8,294,891 B2 | 10/2012 | Mazur et al. |
| 2001/0006869 A1 | 7/2001 | Okamoto et al. |
| 2003/0201717 A1 * | 10/2003 | Hibino et al. ............. 313/586 |
| 2004/0135997 A1 | 7/2004 | Chan |
| 2006/0250613 A1 | 11/2006 | Demuth |
| 2007/0015288 A1 | 1/2007 | Hulteen |
| 2007/0086001 A1 | 4/2007 | Islam |
| 2007/0115469 A1 | 5/2007 | Ebstein |
| 2008/0079104 A1 | 4/2008 | Stewart et al. |
| 2008/0094621 A1 | 4/2008 | Li |
| 2009/0117646 A1 | 5/2009 | Stordeur |
| 2010/0062226 A1 | 3/2010 | Hulteen |
| 2010/0321684 A1 | 12/2010 | Bratkovski |
| 2012/0013903 A1 | 1/2012 | Kuo |
| 2012/0113419 A1 | 5/2012 | Wang |

FOREIGN PATENT DOCUMENTS

| | | |
|---|---|---|
| JP | 2007-240361 A | 9/2007 |
| JP | 2008-035874 A | 2/2008 |
| WO | WO-2006/132224 | 12/2006 |
| WO | WO-2006132224 | 12/2006 |
| WO | WO-2006138442 | 12/2006 |
| WO | WO-2007/011671 | 1/2007 |
| WO | WO-2007011671 | 1/2007 |
| WO | WO-2010056258 | 5/2010 |
| WO | WO-2011014176 | 2/2011 |

OTHER PUBLICATIONS

Application (PCT/US2008/083827), Nov. 17, 2008.
Application (PCT/US2009/052308), Jul. 30, 2009.
Cao et al., Enhanced Raman Scattering from Individual Semiconductor Nanocones and Nanowires, Physical Review Letters PRL 96, 157402 (2006).
Gilles, et al., "UV Nanoimprint Lithography with Rigid Polymer Molds", Microelectronic Engineering 86, (2009), pp. 661-664.
He, et al., "Large-Scale Synthesis of Flexible Free-Standing SERS Substrates with High Sensitivity: Electrospun PVA Nanofibers Embedded with Controlled Alignment of Silver Nanoparticles" ACSNANO vol. 3, No. 12 (2009) pp. 3993-4002.
Hu et al., "Metal Coated Si Nanograss as Highly Sensitive SERS Sensors", Proc. of SPIE, vol. 7312, (2009), pp. 73120I-1-6.
PCT Search Report, PCT/US2008/083827, Aug. 18, 2009.
PCT Search Report, PCT/US2009/052308, Apr. 27, 2010.
Schmidt, et al., "Towards Easily Reproduced Nano-Structured SERS Substrates", IEEE Sensors 2009 Conference, (2009), pp. 1763-1767.
Wu, et al., "One-Kilobit Cross-Bar Molecular Memory Circuits at 30-nm Half-Pitch Fabricated by Nanoimprint Lithography", Springer-Verlar, Pub online, (Mar. 11, 2005), pp. 1173-1178.

* cited by examiner

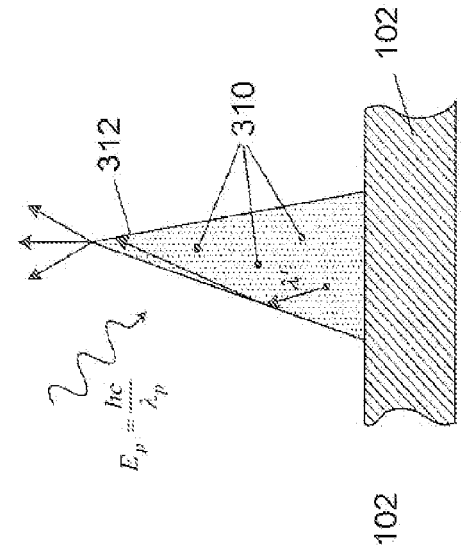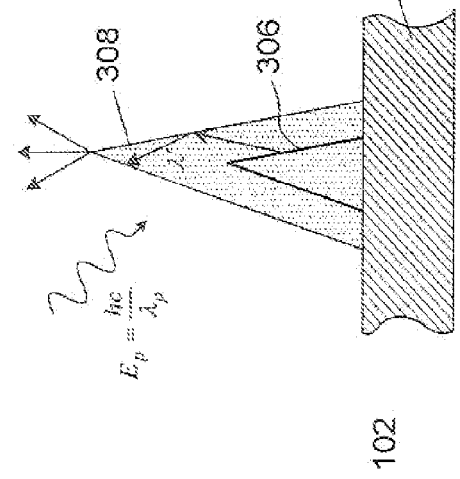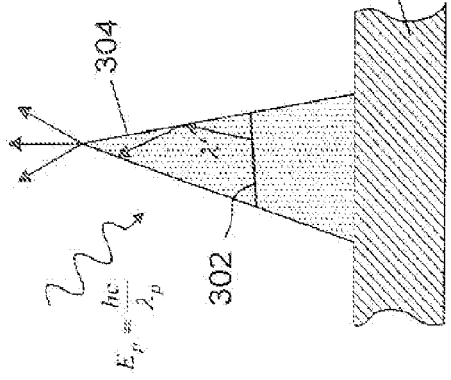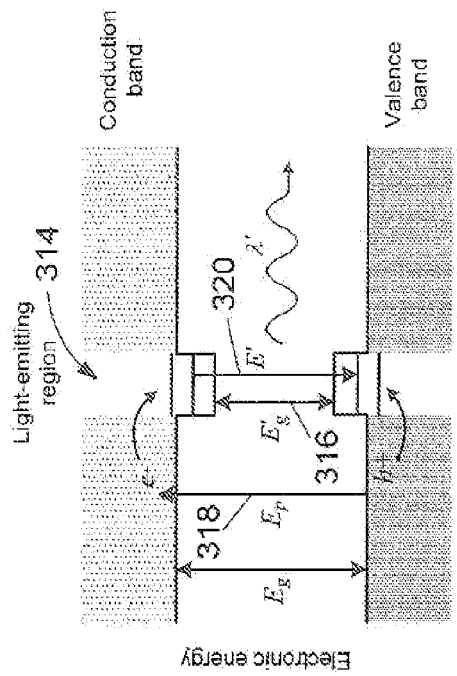

NANOWIRE-BASED SYSTEMS FOR PERFORMING RAMAN SPECTROSCOPY

TECHNICAL FIELD

Embodiments of the present invention relate generally to systems for performing surface-enhanced Raman spectroscopy.

BACKGROUND

Raman spectroscopy is a spectroscopic technique used in condensed matter physics and chemistry to study vibrational, rotational, and other low-frequency modes in molecular systems. In a Raman spectroscopic experiment, a monochromatic beam of light of a particular wavelength range passes through a sample of molecules and a spectrum of scattered light is emitted. The term "light" is not limited to electromagnetic radiation with wavelengths that lie in the visible portion of the electromagnetic spectrum but also includes electromagnetic radiation with wavelengths outside the visible portion, such as the infrared and ultraviolet portions of the electromagnetic spectrum, and can be used to refer to both classical and quantum electromagnetic radiation. The spectrum of wavelengths emitted from the molecule is called a "Raman spectrum" and the emitted light is called "Raman scattered light." A Raman spectrum can reveal electronic, vibrational, and rotational energies levels of a molecule. Different molecules produce different Raman spectrums that can be used like a fingerprint to identify molecules and even determine the structure of molecules.

The Raman scattered light generated by a compound (or ion) adsorbed on or within a few nanometers of a structured metal surface can be $10^3$-$10^6$ times greater than the Raman scattered light generated by the same compound in solution or in the gas phase. This process of analyzing a compound is called surface-enhanced Raman spectroscopy ("SERS"). In recent years, SERS has emerged as a routine and powerful tool for investigating molecular structures and characterizing interfacial and thin-film systems, and even enables single-molecule detection. Engineers, physicists, and chemists continue to seek improvements in systems and methods for performing SERS.

BRIEF DESCRIPTION OF THE DRAWINGS

FIGS. 3A-3C show cross-sectional views of optically pumping light emitters of tapered nanowires in accordance with embodiments of the present invention.

FIG. 3D shows an exemplary electronic energy band diagram associated with a light emitter of a tapered nanowire operated in accordance with embodiments of the present invention.

DETAILED DESCRIPTION

Embodiments of the present invention are directed to nanowire-based systems for performing surface-enhanced Raman spectroscopy. The systems include an array of tapered nanowires disposed on a substrate. The tapered nanowires are configured with gain, and SERS-active nanoparticles are disposed on the outer surface of the tapered nanowires and, in certain embodiments, near the tapered ends, or tips, of the tapered nanowires. With electronic or optical pumping, the nanowires emit Raman excitation light. The tapered nanowires are configured to direct a substantial portion of the Raman excitation light emitted with the nanowires toward the tapered ends of the nanowires to interact with the SERS-active nanoparticles and enhance the Raman spectrum of molecules disposed on or near the SERS-active nanoparticles.

I. Optically Operated SERS-Active Systems

Figure 1A:
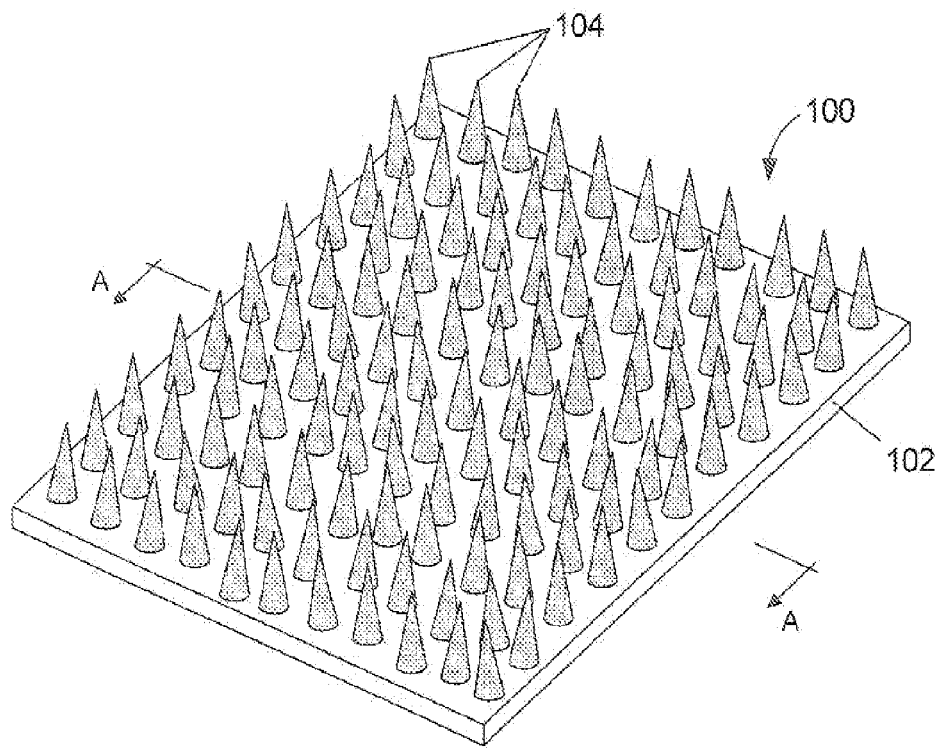
FIG. 1A shows an isometric view of a first surface-enhanced Raman spectroscopy ("SERS")-active system configured in accordance with embodiments of the present invention.

FIG. 1A shows an isometric view of a SERS-active system 100 configured in accordance with embodiments of the present invention. The system 100 includes a substrate 102 and a plurality of tapered nanowires 104 disposed on a surface of the substrate 102. As shown in the example of FIG. 1A, the nanowires 104 are configured to taper away from the substrate 102 and may be randomly distributed.

Figure 1B:
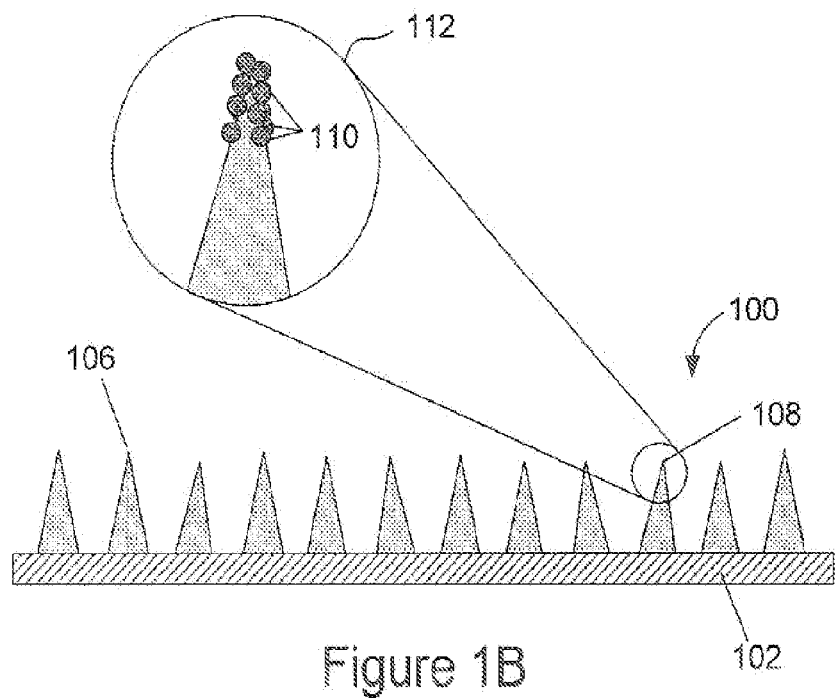
FIG. 1B shows a cross-sectional view along a line A-A, shown in FIG. 1A, of the first SERS-active system configured in accordance with embodiments of the present invention.

FIG. 1B shows a cross-sectional view along a line A-A, shown in FIG. 1A, of the system 100 in accordance with embodiments of the present invention. In the example of FIG. 1B, the tapered nanowires may have a symmetric, inverted-cone shape, such as tapered nanowire 106, or an asymmetric, inverted-cone shape, such as tapered nanowire 108. The system 100 also includes SERS-active nanoparticles disposed near the tapered end, or tip, of the nanowires. In FIG. 1B, the tapered end of nanowire 108 is magnified in an enlargement 112 revealing a plurality of SERS-active nanoparticles 110 disposed on the outer surface, near the tip, of the nanowire 108. Note that embodiments of the present invention are not limited to nanoparticles disposed over just the tip of the nanowires. In other embodiments, the nanoparticles can be disposed over nearly the entire surface of the nanowires.

The substrate 102 can be composed of a dielectric material, including glass, $SiO_2$, $Al_2O_3$, or any other suitable material, such as a metal or semiconductor. The tapered nanowires 104 can be composed of materials enabling the nanowires to be operated as gain media when the SERS-active system 100 is optically pumped. For example, the nanowires can be composed of a direct or an indirect semiconductor material. Direct semiconductors are characterized by the valence band maximum and the conduction band minimum occurring at approximately the same wavenumber. As a result, an electron in the conduction band recombines with an unoccupied electronic state in the valence band giving off the energy difference as a photon of light. In contrast, indirect semiconductors are characterized by the valence band maximum and the conduction band minimum occurring at different wavenumbers. An electron in the conduction band minimum recombines with an unoccupied electronic state in the valence band maximum by first undergoing a momentum change followed by a change in electronic energy.

Indirect and direct semiconductors can be elemental and compound semiconductors. Indirect elemental semiconductors include silicon (Si) and germanium (Ge), and compound semiconductors include III-V materials, where Roman numerals III and V represent elements in the Ma and Va columns of the Periodic Table of the Elements. Compound semiconductors can be composed of column Ma elements, such as aluminum (Al), gallium (Ga), and indium (In), in combination with column Va elements, such as nitrogen (N), phosphorus (P), arsenic (As), and antimony (Sb). Compound semiconductors can also be further classified according to the relative quantities of III and V elements. For example, binary semiconductor compounds include GaAs, InP, InAs, and GaP; ternary compound semiconductors include $GaAs_yP_{1-y}$, where y ranges from greater than 0 to less than 1; and quaternary compound semiconductors include $In_xGa_{1-x}As_yP_{1-y}$, where both x and y independently range from greater than 0 to less than 1. Other types of suitable compound semiconductors include II-VI materials, where II and VI represent elements in the IIb and VIa columns of the periodic table. For example, CdSe, ZnSe, ZnS, and ZnO are examples of binary II-VI compound semiconductors.

The tapered nanowires can be formed using a vapor-liquid-solid ("VLS") chemical synthesis process. This method typically involves depositing particles of a catalyst material such as gold or titanium on a surface of the substrate 102. The substrate 102 is placed in a chamber and heated to temperatures typically ranging between about 250° C. to about 1000° C. Precursor gasses including elements or compounds that will be used to form the nanowires are introduced into the chamber. The particles of the catalyst material cause the precursor gasses to at least partially decompose into their respective elements, some of which are transported on or through the particles of catalyst material and deposited on the underlying surface. As this process continues, nanowires grow with the catalyst particle remaining on the tip or end of the nanowires. Nanowires can also be formed by physical vapor deposition, by surface atom migration, or etched back by reactive etching with or without a lithographically defined masking pattern The nanowire material can be selected to emit Raman excitation light with Raman excitation wavelengths, $\lambda'$, that the enhance Raman spectrum of molecules located at or near the SERS-active nanoparticles when the nanowires are optically pumped with light of an appropriate pump wavelength $\lambda_p$. FIG. 2A shows optically pumping a tapered nanowire 202 in accordance with embodiments of the present invention. In FIG. 2A, tapered nanowire 202 is illuminated with light having a pump wavelength $\lambda_p$ and corresponding energy $E_p$:

$$E_p = \frac{hc}{\lambda_p}$$

where h is Planck's constant, and c is the speed of light in free space.

Figure 2B:
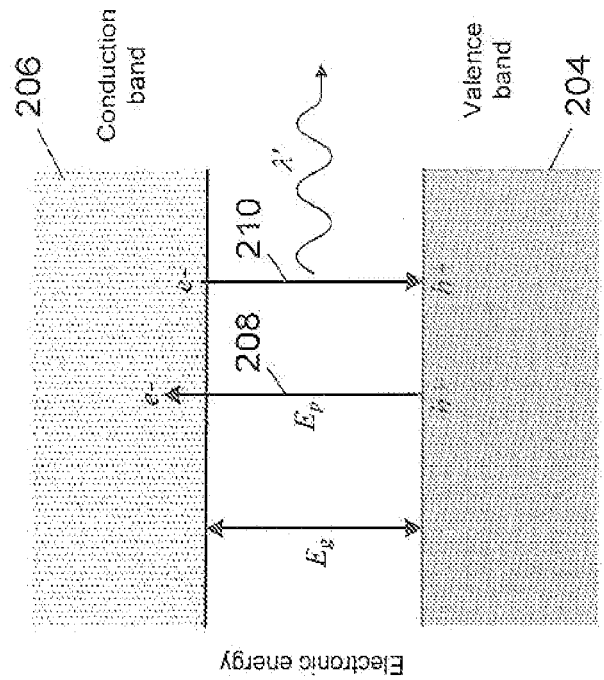
FIG. 2B shows an exemplary electronic energy band diagram for the tapered nanowire, shown in FIG. 2A, operated in accordance with embodiments of the present invention.
Figure 2A:
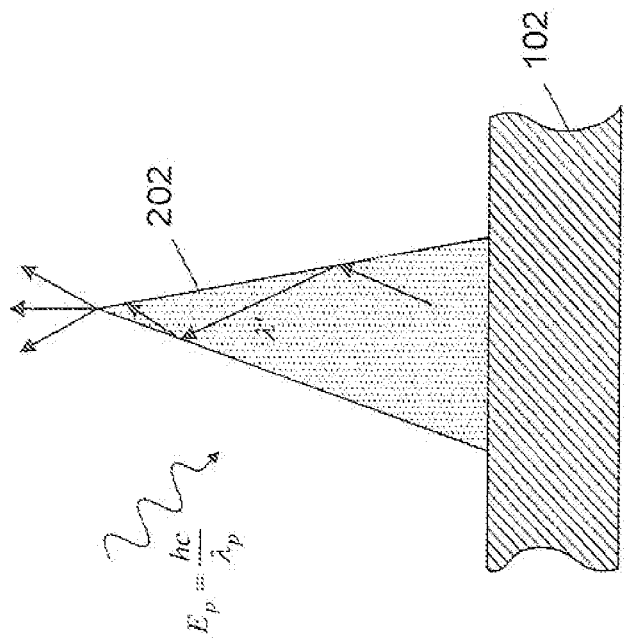
FIG. 2A shows optically pumping a tapered nanowire in accordance with embodiments of the present invention.

FIG. 2B shows an exemplary electronic energy band diagram associated with a tapered nanowire in accordance with embodiments of the present invention. In FIG. 2B, heavily shaded region 204 represents a mostly filled continuum of electronic energy states and lightly shaded region 206 represents a mostly vacant continuum of unoccupied electronic energy states called "holes" which act like positive charge carriers. Electrons and holes are called "charge carriers." As shown in the example of FIG. 2B, optically pumping a nanowire, such as nanowire 202, with light of photon energy $E_p$ 208 exceeding the band gap energy $E_g$ of the nanowire material (i.e., $E_p > E_g$), causes electrons (e−) to be excited from near the top of the valence band into electronic energy states in the conduction band, leaving holes (h+) near the top of the valence band. An electron excited into the conduction band may relax via thermal processes to a relatively lower electronic energy state in the conduction band, where the electron remains until the electron spontaneously recombines with a hole in the valence band and emits a photon of light with Raman excitation wavelength $\lambda'$ and corresponding energy E' 210 satisfying the condition:

$$E_p > E' = \frac{hc}{\lambda'} \geq E_g$$

In other embodiments, the material comprising the tapered nanowires can be doped with impurity atoms that introduce one or more metastable states into the electronic band gap near the bottom of the conduction band from which excited electrons transition to and remain for a short period of time before spontaneously recombining with holes in the valence band. The impurities can be selected to emit Raman excitation light with Raman excitation wavelengths $\lambda'$.

Returning to FIG. 2A, the light emitted from the nanowire 202 may be trapped by internal reflection within the nanowire 202 due to the contrast between the refractive index of the nanowire 202 material and the relatively lower refractive index of the surrounding air. As a result, a substantial portion of the emitted light may be reflected off of the interior walls within the nanowire, directed toward the tip of the nanowire, and emitted near the tip of the nanowire, as shown in FIG. 2A. The light produced by the spontaneous emission may also stimulate the emission of more Raman excitation light, and the stimulated emissions further stimulates the emission of even more Raman excitation light. The light continues to build-up and may constructively interfere to produce amplified light with the Raman excitation wavelengths $\lambda'$ emitted near the tip of the nanowire 202.

In other embodiments, the tapered nanowires can be configured with one or more light emitters, including quantum wells ("QWs") or light-emitting particles, such as quantum dots ("QDs"), atoms or molecules, that can be selected and dimensioned to emit Raman excitation light with Raman excitation wavelengths $\lambda'$. FIG. 3A shows a cross-sectional view of optically pumping a QW 302 embedded in a tapered nanowire 304 in accordance with embodiments of the present invention. The QW 302 is a layer oriented substantially parallel to the surface of the substrate 102. FIG. 3B shows a cross-sectional view of optically pumping a core-shell QW 306 embedded within a tapered nanowire 308 in accordance with embodiments of the present invention. In other embodiments, rather than an embedded core-shell QW, as shown in FIG. 3B, the QW can be a shell located on at least a portion of the outer surface of the nanowire 308. FIG. 3C shows optically pumping light-emitting particles 310 embedded within a tapered nanowire 312 in accordance with embodiments of the present invention.

The electronic band gap of QDs and QWs can be determined by the size of the QDs or thickness of the QWs in addition to the type of materials selected for the QDs and QWs. In other words, the Raman excitation wavelength $\lambda'$ can be obtained by appropriate selection of the size of the QDs, thickness of the QWs, and the QD or QW materials. In certain embodiments, for example, QDs or QW can be composed of GaAs and the remaining tapered nanowire can be composed of AlGaAs; or for example, QDs or QW can be composed of InGaAsP and the remaining tapered nanowire can be composed of InP. The QWs can be unstrained in which the lattice constant for the QWs nearly matches the lattice constant of the remaining nanowire. Examples of unstrained QWs include a GaAs QW that substantially matches the lattice of a $Al_{0.2}Ga_{0.8}As$ bulk material, and the same situation occurs for a $In_{1-x}Ga_xAs_yP_{1-y}$ QW in bulk InP when $x \approx 0.45y$. In other embodiments, particular atoms and molecules can be selected for the light-emitting particulars to emit the Raman excitation wavelength $\lambda'$.

FIG. 3D shows an exemplary electronic energy band diagram associated with a light emitter of a tapered nanowire in accordance with embodiments of the present invention. In FIG. 3D, region 314 represents the quantum states associated with the light emitter, such as the light emitters shown in FIGS. 3A-3C. The light emitter has a smaller electronic band gap, denoted by $E'_g$ 316, than the electronic band gap $E_g$ of the remaining nanowire (i.e., $E_g > E'_g$). Optically pumping the nanowires with light having photon energy:

$$E_p = \frac{hc}{\lambda_p}$$

where $E_p > E_g$, excites electrons from near the top of the valence band into electronic energy states in the conduction band. Electrons in the conduction band are free to migrate into the relatively lower energy quantized conduction band states of the light emitter 314, and holes migrate to the relatively higher energy quantized valence band states of the light emitter. As represented in FIG. 3D, electrons in the conduction band of the light emitter 314 spontaneously recombine with holes in the valence band of the light emitter 314 emitting photons of light with Raman excitation wavelengths $\lambda'$ and corresponding energies E' 320 satisfying:

$$E_p > E' = \frac{hc}{\lambda'} \geq E'_g$$

As shown in FIGS. 3A-3C, the light emitted from the light emitters of the nanowires 304, 308 and 312 can be trapped by internal reflection within the nanowires due to the contrast between the refractive index of the nanowire material and the relatively lower refractive index of the surrounding air. As a result, a substantial portion the emitted light is directed toward, and emitted from, near the tip of the nanowires. The Raman excitation light produced by the spontaneous emission may also stimulate the emission of more Raman excitation light from the light emitters with the Raman excitation wavelengths $\lambda'$, and the stimulated emissions further stimulates the emission of even more light with wavelengths $\lambda'$. The Raman excitation light can continue to build-up and may constructively interfere to produce amplified light with the Raman excitation wavelengths $\lambda'$ released near the tip of the nanowires.

Returning to FIGS. 1A-1B, the SERS-active system 100 can be used to identify one or more analyte molecules by selecting the composition of the tapered nanowire or light emitters to emit Raman excitation wavelengths $\lambda'$ causing the analytes to produce associated Raman spectra of Raman scattered light. Each Raman spectrum can be detected and used to identify each of the analytes. The SERS-active nanoparticles 110 deposited near the tip of the nanowires can be composed of silver ("Ag"), gold ("Au"), copper ("Cu") or another metal suitable for forming a structured metal surface that when illuminated by the Raman excitation wavelengths $\lambda'$ enhances the intensity of the Raman scattered light.

Figure 4:
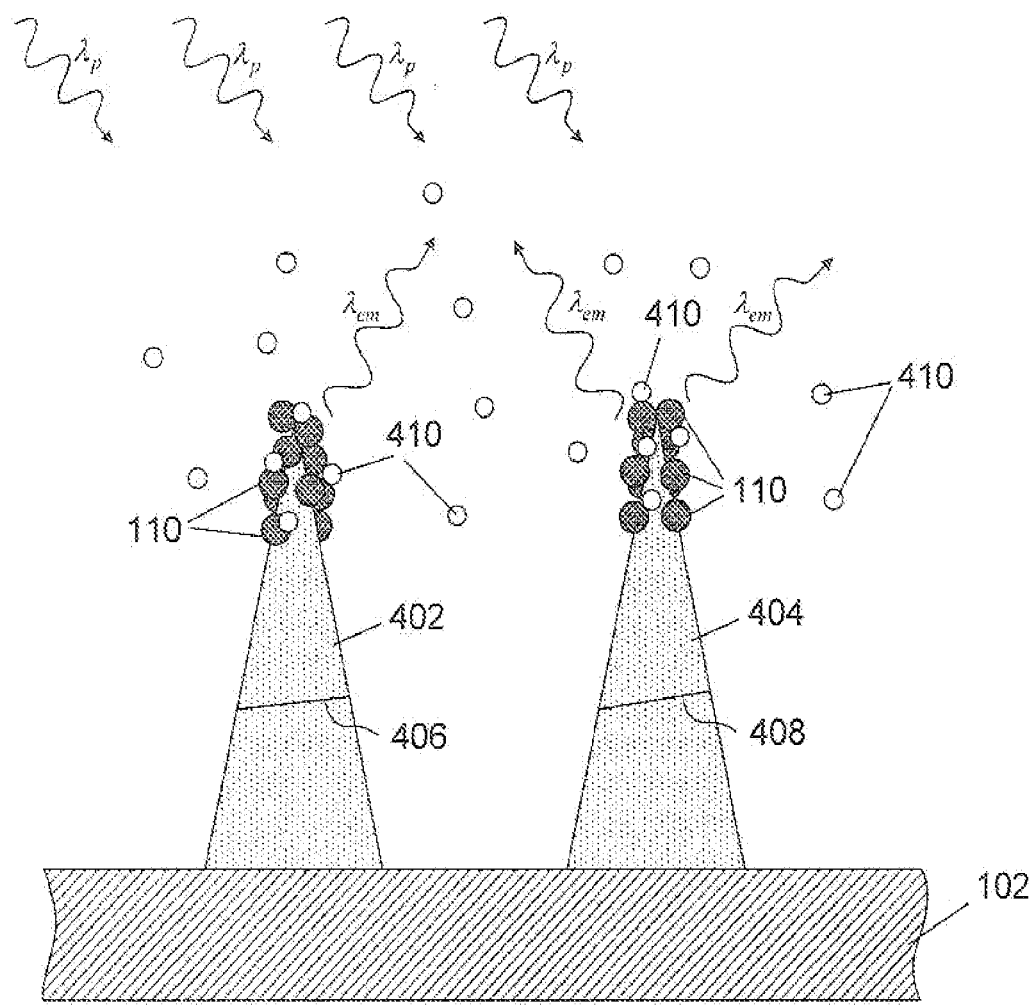
FIG. 4 shows a cross-sectional view of two tapered nanowires of an optically operated SERS-active system in accordance with embodiments of the present invention.

FIG. 4 shows a cross-sectional view of two tapered nanowires 402 and 404 of an optically pumped SERS-active system operated in accordance with embodiments of the present invention to produce a Raman spectrum. The nanowires 402 and 404 are each configured with a single QW layer 406 and 408, respectively, as described above with reference to FIG. 3A. As shown in FIG. 4, an analyte 410 is introduced and the nanowires 402 and 404 are optically pumped with light having a pump wavelength $\lambda_p$ that causes the emission of Raman excitation light with Raman excitation wavelengths from the layers 406 and 408. As described above with reference to FIGS. 3A and 3D, the light is substantially confined within, and emitted near the tip of, the nanowires 402 and 404. The Raman excitation wavelengths cause analytes 410 located near the tips of the nanowires 402 and 404 to produce a Raman spectrum of Raman scattered light over a range wavelengths denoted by $\lambda_{em}$. The intensity of the Raman scattered light may also be enhanced as a result of two mechanisms. The first mechanism is an enhanced electromagnetic field produced at the surface of the SERS-active nanoparticles 110. The materials and thickness of the QWs 406 and 408 can also be selected so that the Raman excitation wavelengths $\lambda'$ are close to the plasma wavelength of the nanoparticles 110. As a result, conduction electrons in the metal surfaces of the nanoparticles 110 are excited into an extended surface excited electronic state called a "surface plasmon polariton." Analytes 410 adsorbed on or in close proximity to the nanoparticles 110 experience a relatively strong electromagnetic field. Molecular vibrational modes directed normal to the nanoparticle 110 surfaces are most strongly enhanced. The intensity of the surface plasmon polariton resonance depends on many factors including the wavelength of the Raman excitation light λ' emitted from the QWs 406 and 408 and the morphology of the nanoparticles 110. The second mode of enhancement, charge transfer, may occur as a result of the formation of a charge-transfer complex between the surfaces of the nanoparticles 110 and the analyte 410 absorbed to these surfaces. The electronic transitions of many charge transfer complexes are typically in the visible range of the electromagnetic spectrum.

Note that the SERS-active system 100 can be implemented with any one of the tapered nanowires represented in FIGS. 2A and 3A-3C and are not limited to nanowires having a single QW layer. In other embodiments, the tapered nanowires can have two or more QW layers.

Figure 5:
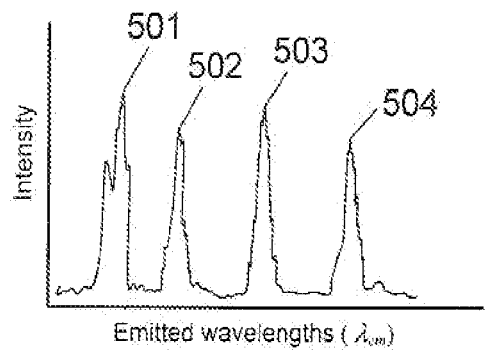
FIG. 5 shows an example Raman spectrum.

FIG. 5 shows an example Raman spectrum associated with Raman scattered light. In the example of FIG. 5, the Raman spectrum comprises four intensity peaks 501-504, each peak corresponding to a particular frequency. The intensity peaks 501-504 and associated wavelengths can be used like a finger print to identify the associated analyte.

II. Electronically Operated SERS-Active Systems

Figure 6A:
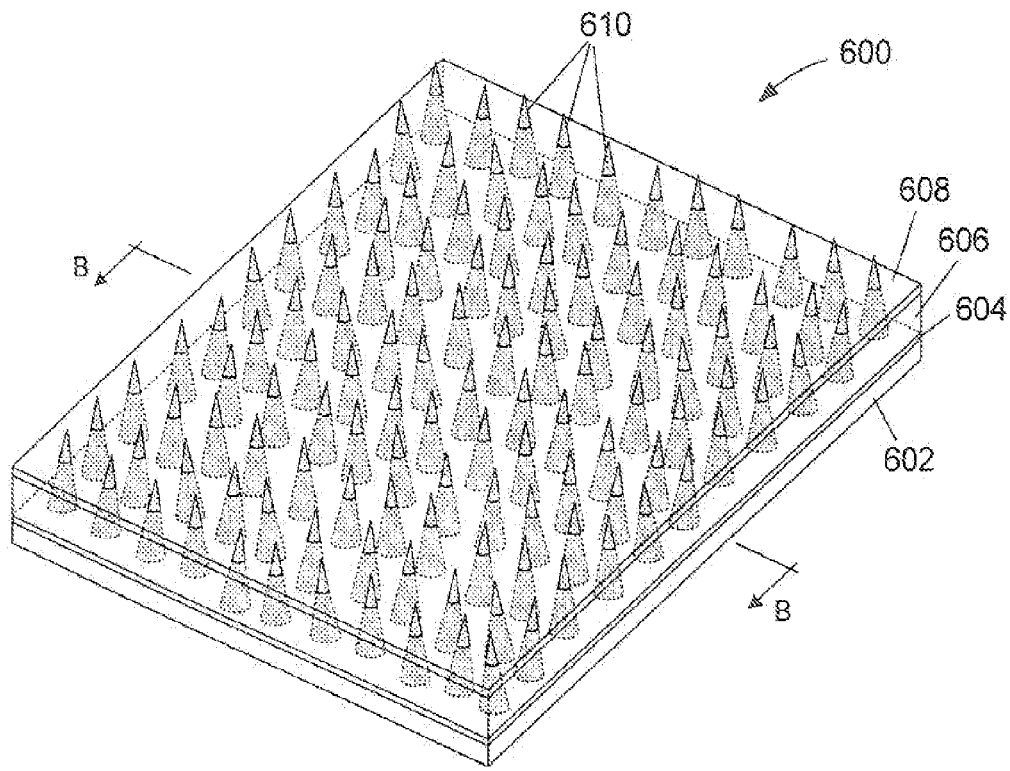
FIG. 6A shows an isometric view of a second SERS-active system configured in accordance with embodiments of the present invention.

FIG. 6A shows an isometric view of a SERS-active system 600 configured in accordance with embodiments of the present invention. As shown in FIG. 6A, the system 600 includes a substrate 602, a first electrode layer 604 disposed on the substrate 602, a dielectric layer 606 disposed on the first electrode layer 604, and a second electrode layer 608 disposed on the dielectric layer 606. The system also includes a plurality of tapered nanowires 610 disposed on the first electrode layer 604 and embedded within the dielectric layer 606 with the nanowire tapered ends, or tips, extending above the second electrode layer 608. As shown in the example of FIG. 6A, the nanowires 610 tapered ends are directed away from the substrate 602 and that nanowires 610 may be randomly distributed.

Figure 6B:
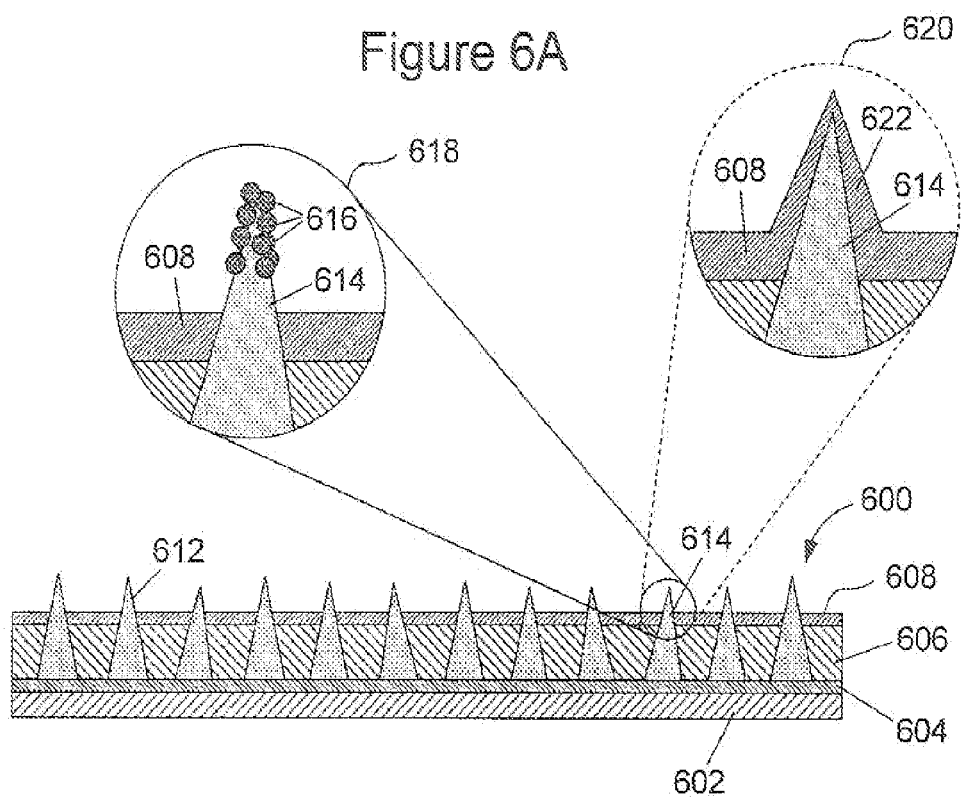
FIG. 6B shows a cross-sectional view along a line B-B, shown in FIG. 6A, of the second SERS system configured in accordance with embodiments of the present invention.

FIG. 6B shows a cross-sectional view along a line B-B, shown in FIG. 6A, of the system 600 in accordance with embodiments of the present invention. In the example of FIG. 6B, the tapered nanowires 610 may have a symmetric inverted-cone shape, such as tapered nanowire 612, or an asymmetric inverted-cone shape, such as tapered nanowire 614. The system 600 can be configured to also include SERS-active nanoparticles disposed near the tip of the nanowires. In FIG. 6B, the end of tapered nanowire 614 is magnified in an enlargement 618 revealing a number of SERS-active nanoparticles 616 disposed on the outer surface, near the tip, of the nanowire 614. FIG. 6B also shows an enlargement 620 of the nanowire 614, which represents a second embodiment where, rather than coating the tips of the nanowires with SERS-active nanoparticles, a thin portion 622 of the second electrode layer 608 covers at least a portion of the nanowire 614 tip.

The substrate 602 can be composed of a dielectric material, including glass, $SiO_2$, $Al_2O_3$, or a suitable metal or semiconductor. The first and second electrode layers 604 and 606 can be composed of Ag, Au, Cu, or any other suitable electrical conducting material. The first electrode 604 can be formed on the substrate 602 using chemical vapor deposition ("CVD") or wafer bonding. The nanowires 610 can be formed using VLS described above with reference to FIG. 1. The dielectric layer 606 can be composed of glass, $SiO_2$, $Al_2O_3$, or any other suitable dielectric material and can be formed around the nanowires 610 using a spin-on-glass technique. The second electrode layer 608 can be formed on the dielectric layer 606 using CVD and etched away around the nanowires so that SERS-active nanoparticles 616 can be deposited using CVD, as shown in the enlargement 618 in FIG. 6B, or, in another embodiment, the second electrode layer 608 can remain leaving a thin layer of conductive material on the tips of the nanowires, as shown in the enlargement 620 in FIG. 6B.

Figure 7A:
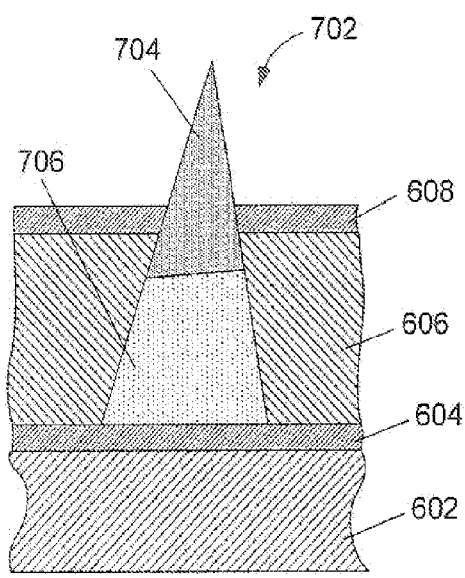
FIGS. 7A-7B show cross-sectional views of exemplary pn and p-i-n junction tapered nanowires, respectively, configured in accordance with embodiments of the present invention.
Figure 7B:
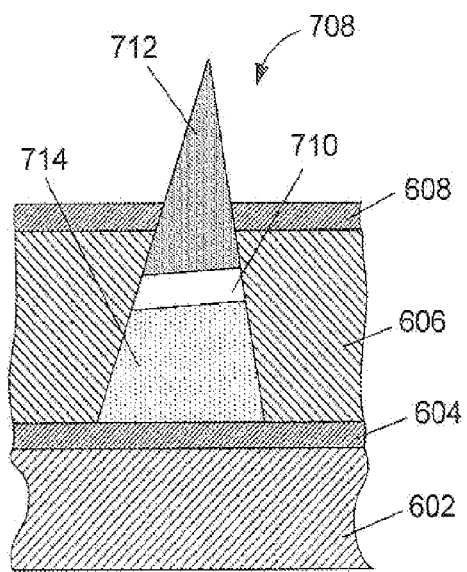

The tapered nanowires of the SERS-active system 600 can also be configured as pn or p-i-n junctions and electronically pumped to generate Raman excitation light. FIG. 7A shows a cross-sectional view of an exemplary pn junction tapered nanowire 702 configured in accordance with embodiments of the present invention. The tapered nanowire 702 includes an n-type layer 704 and an adjacent p-type layer 706. FIG. 7B shows a cross-sectional view of an exemplary p-i-n junction tapered nanowire 708 configured in accordance with embodiments of the present invention. The tapered nanowire 708 includes an intrinsic semiconductor layer 710 sandwiched between an n-type layer 712 and a p-type layer 714. Note that in other embodiments the n-type and p-type layers can be reversed.

The p-type layers 706 and 714 are doped with impurity or electron acceptor atoms having fewer electrons than the atoms they replace in the semiconductor compound, which creates holes, or vacant electronic energy states, in the valence band of the p-type layers 706 and 714. On the other hand, the n-type layers 704 and 712 are doped with impurities or electron donor atoms that donate electrons to the semiconductor, which leaves extra electrons in the electronic energy states of the conduction band of the n-type layers 704 and 712. For nanowire 702, a depletion layer (not shown) forms between the n-type and p-type layers 704 and 706 as a result of the difference in chemical potential between the p-type and n-type semiconductor layers. For nanowire 708, the n-type and p-type layers 712 and 714 can be composed of wider (direct or indirect) electronic band gap semiconductors while the intrinsic layer 710 can be composed of a relatively narrower, direct band gap semiconductor, thus forming a double heterostructure p-i-n junction.

The n-type and p-type semiconductors layers of the tapered nanowires 702 and 708 are formed by doping layers of the tapered nanowires with appropriate impurities during formation of the nanowires. For example, n-type III-V compound semiconductors are formed by introducing column VI impurities, such as sulfur (S), selenium (Se), and tellurium (Te), to occupy column V sites in the III-V lattice and serve as electron donors. P-type III-V compound semiconductors are formed by introducing column II impurities, such as beryllium (Be), zinc (Zn), and cadmium (Cd), to occupy column III sites in the III-V lattice and serve as electron acceptors. Si and Ge can serve as either electron donors or acceptors depending on whether they occupy column III sites or column V sites, respectively. An n-type layer in Si and Ge nanowires are created by column V impurities that serves as electron donors, and a p-type layer in Si and Ge nanowires are created by column III impurities that serve as electron acceptors.

Figure 8A:
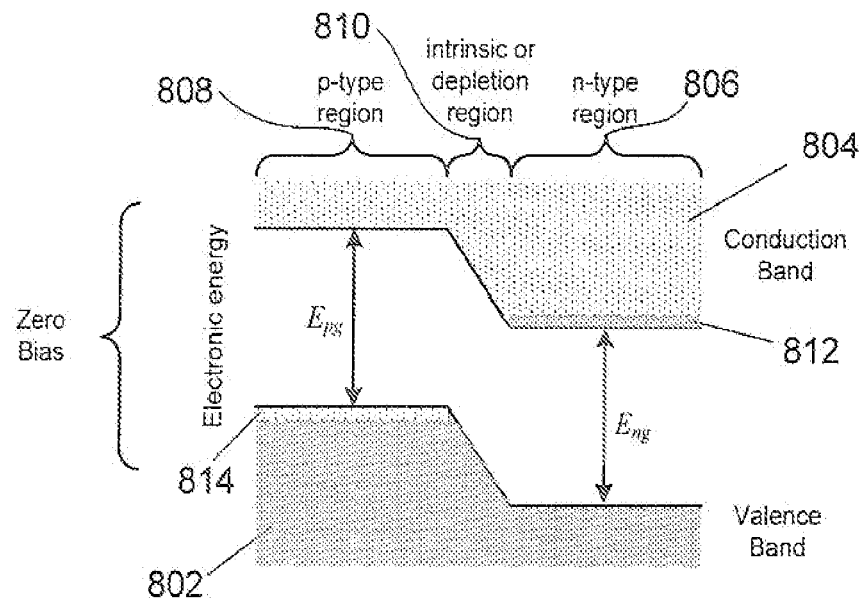
FIGS. 8A-8B show electronic energy band diagrams for pn and p-i-n junction tapered nanowires operated in accordance with embodiments of the present invention.
Figure 8B:
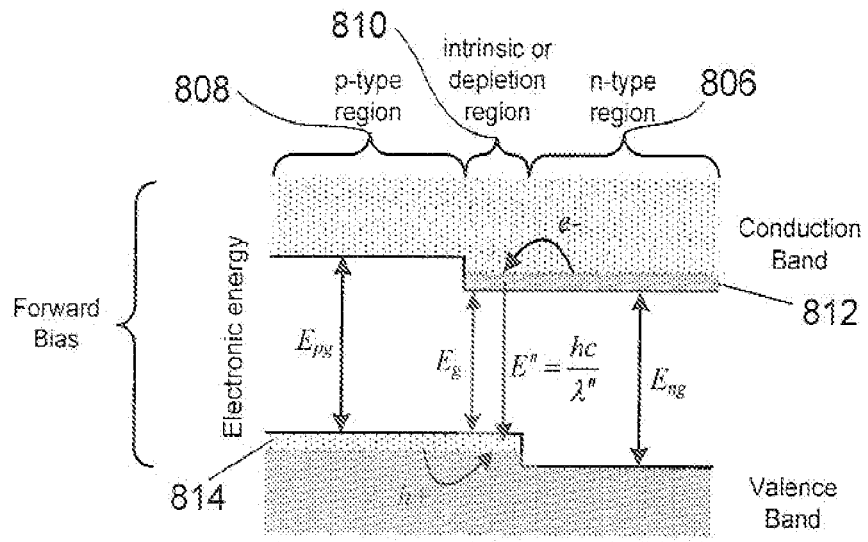

FIGS. 8A-8B show electronic energy band diagrams associated with pn and p-i-n junction tapered nanowires. Heavily shaded regions, such as region 802, represent mostly filled electronic energy states and lightly shaded regions, such as region 804, represent mostly vacant electronic energy states or holes. As shown in the band diagrams of FIG. 8A-8B, an n-type region 806 corresponds to an n-type layer, p-type region 808 corresponds to a p-type layer, and intrinsic or depletion region 810 corresponds to a depletion region or an intrinsic layer of pn junction or p-i-n junction nanowires, such as nanowires 702 and 708. Electron donor impurities create substantially filled electronic states 812 near the conduction band of the n-type region 806 while electron acceptors create electronic states 814 near the valence band of the p-type region 808. As shown in FIG. 8A, the valence and conduction bands associated with the p-type region 808 are higher in electronic energy than the valence and conduction bands associated with n-type region 806. Depending on the size of the band gap energies associated with the regions 806 and 808, some electrons can be thermally excited into mostly empty conduction bands as indicated by region 812. FIG. 8A also reveals steep conduction and valence bands associated with the region 810 which prevent holes and electrons from migrating between the neighboring p- and n-type regions 806 and 808, respectively. However, as shown in FIG. 8B, when a forward bias is applied to the associated nanowire, electrons are injected into the n-type region 806 and holes are injected into the p-type region 808, changing the electronic energy band diagram. In FIG. 8B, the steep potential associated with the region 810 flattens. Electrons are injected into the conduction band of the region 810 from the n-type region 806, while holes are injected into the valence band of the region 810 from the p-type region 808. As shown in FIG. 8B, the regions 806 and 808 have relatively higher electronic band gap energies $E_{ng}$ and $E_{pg}$ than the band gap energy $E_g$ of the region 810, which confines the injected carriers to the region 810, where electrons can spontaneously recombine from electronic states near the bottom of the conduction band of the region 810 with holes in electronic states near the top of the valence band of the region 810, emitting photons of light, each photon having an energy:

$$E'' = \frac{hc}{\lambda''} \geq E_g$$

where $\lambda''$ represents the Raman excitation wavelength.

As long as an appropriate voltage is applied in the same forward bias direction, electrons and holes flow through the nanowire and spontaneously recombine at the region 810, and light is emitted with the wavelength $\lambda''$ in the nanowire. As described above with reference to FIG. 2A, a substantial portion of the emitted light is trapped within the nanowire by internal reflection due the nanowire having a relatively larger refractive index than the dielectric layer 606. The trapped light is internally reflected toward the tip of the nanowire where the light is emitted.

Figures 9A, 9B:
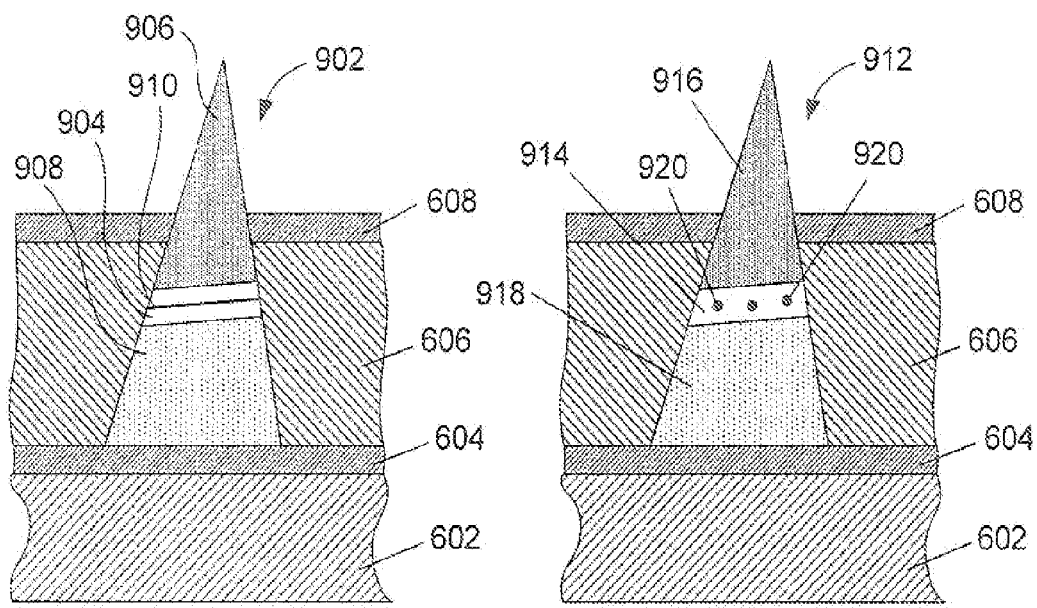
FIG. 9A shows a cross-sectional view of a p-i-n junction tapered nanowire including a quantum well configured in accordance with embodiments of the present invention.
FIG. 9B shows a cross-sectional view of a p-i-n junction tapered nanowire including light-emitting particles configured in accordance with embodiments of the present invention.

In other embodiments, p-i-n junction tapered nanowires can also be configured to include a light emitter embedded within the intrinsic layer. The light emitter can be one or more QWs or light-emitting particles, including QDs, atoms or molecules. FIG. 9A shows a cross-sectional view of a first p-i-n junction tapered nanowire 902 configured in accordance with embodiments of the present invention. The nanowire 902 comprises an intrinsic layer 904 sandwiched between an n-type layer 906 and a p-type layer 908. As shown in FIG. 9A, the intrinsic layer 904 also includes a QW 910. FIG. 9B shows a cross-sectional view of a second p-i-n junction tapered nanowire 912 configured in accordance with embodiments of the present invention. The nanowire 912 comprises an intrinsic layer 914 sandwiched between an n-type layer 916 and a p-type layer 918. As shown in FIG. 9B, the intrinsic layer 914 also includes light emitters 920.

Figure 10A:
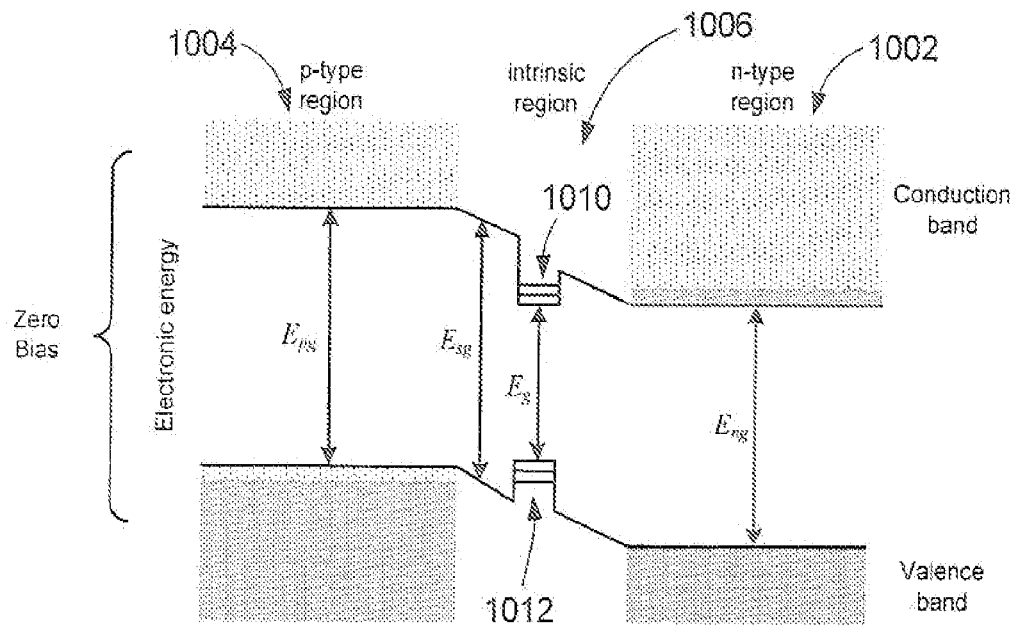
FIGS. 10A-10B show electronic energy band diagrams for a p-i-n junction tapered nanowire configured with a light emitter and operated in accordance with embodiments of the present invention.
Figure 10B:
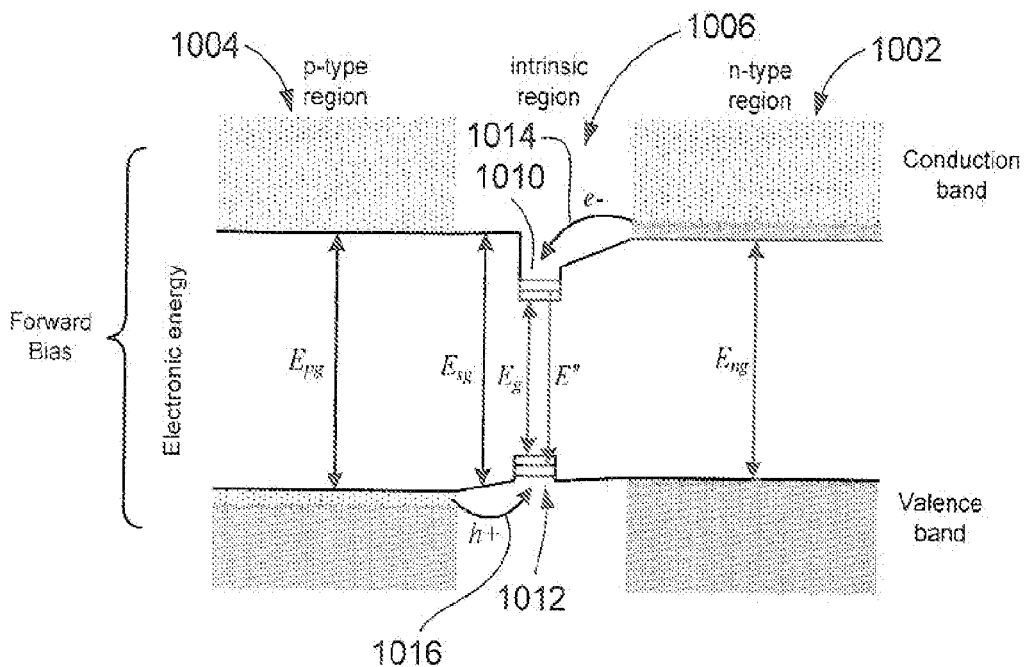

FIGS. 10A-10B show electronic energy band diagrams for a p-i-n junction tapered nanowire configured with a light emitter in accordance with embodiments of the present invention. As described above with reference to FIG. 8, heavy and light shaded regions correspond to filled and substantially unfilled electronic energy states. N-type region 1002 corresponds to an n-type layer, p-type region 1004 corresponds to a p-type layer, and intrinsic region 1006 corresponds to an intrinsic layer of a p-i-n junction tapered nanowire, such as nanowires 902 and 912. As shown in FIGS. 10A and 10B, the intrinsic region 1006 includes quantized electronic energy states associated with a light emitter, such as QW 910 and nanoparticles 920 embedded within intrinsic regions 904 and 914. At zero bias, the light emitter has a relatively low concentration of electrons in the associated quantized conduction band 1010 and a relatively low number of holes in the associated quantized valence band 1012. FIG. 10A also reveals that the semiconductor materials selected for the tapered nanowire layers may have different associated electronic band gaps. In particular, the electronic band gap energy $E_{ng}$ of the n-type region 1002, the electronic band gap energy $E_{pg}$ of the p-type region 1004, and the electronic band gap $E_{sg}$ of the intrinsic region 1006 are greater than the electronic band gap energy $E_g$ of the light emitter.

FIG. 10B shows an electronic energy-band diagram associated with a p-i-n junction tapered nanowire under an applied forward-bias operating voltage in accordance with embodiments of the present invention. Under a forward-bias operating voltage, electrons are injected from the voltage source into the conduction band of the n-type layer, and holes are injected into the valence band of the p-type layer. As a result, the electronic energy associated with the valence and conduction bands of the p-type region 1004 are lowered relative to the valence and conduction bands of the n-type region 1002. The strength of the electric field across the light emitter is reduced or eliminated and electrons are injected 1014 from the conduction band of the n-type region 1002 into the conduction band electronic energy levels 1010, while holes are injected 1016 from the valence band of the p-type region 1004 into the valence band electronic energy levels 1012, resulting in a high density of electrons in the conduction band energy levels 1010 and a corresponding high density of holes in the valence band energy levels 1012. The relatively higher electronic band gap energies $E_{ng}$, $E_{pg}$, and $E_{sg}$ confine the injected carriers to the respective energy levels 1010 and 1012. As long as an appropriate voltage is applied in the forward-bias direction, electrons and holes can spontaneously recombine emitting photons with Raman excitation wavelengths $\lambda''$ satisfying the condition:

$$E_{ng}, E_{pg}, \text{ and } E_{sg} > E'' = \frac{hc}{\lambda''} \geq E_g$$

Figure 11:
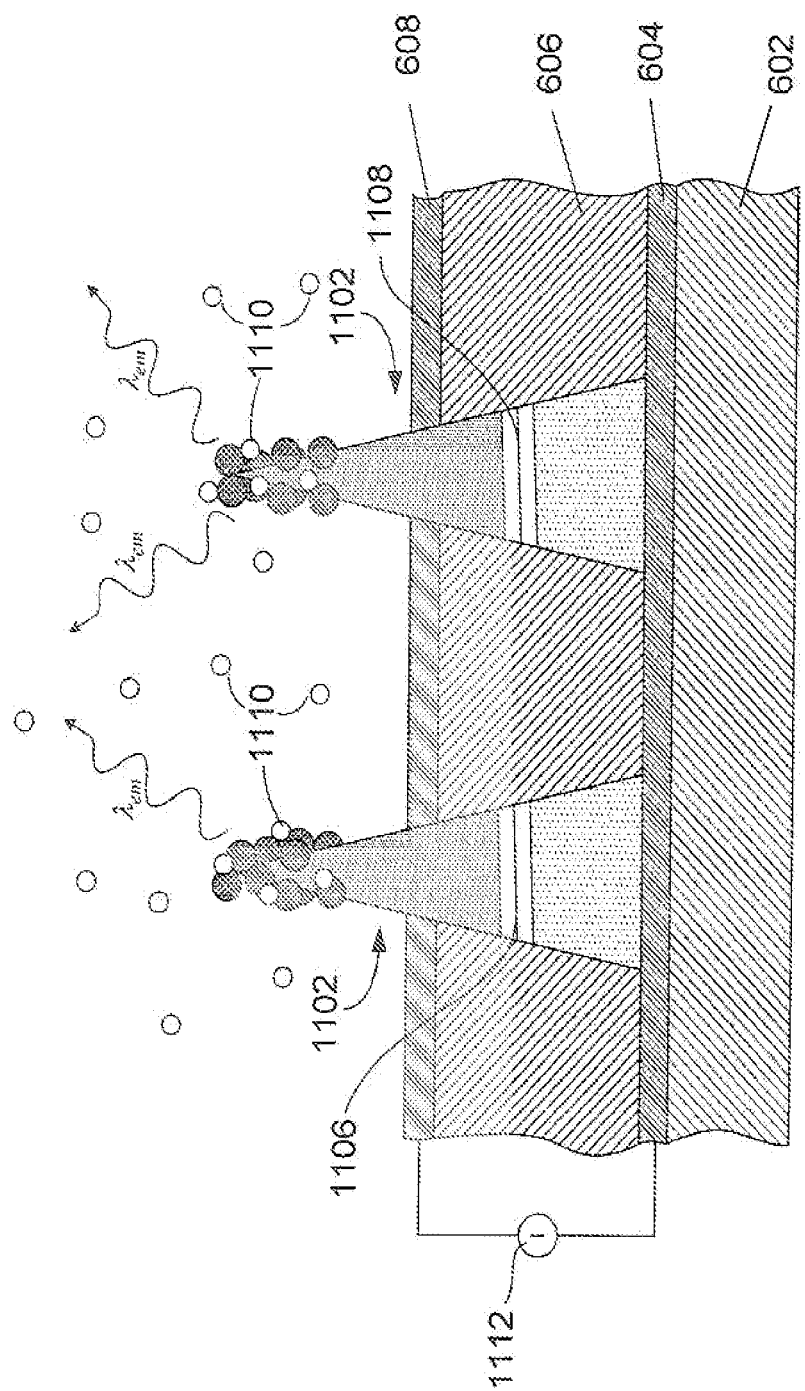
FIG. 11 shows a cross-sectional view of two tapered nanowires of an electronically operated SERS-active system in accordance with embodiments of the present invention to produce a Raman spectrum.

FIG. 11 shows a cross-sectional view of two tapered nanowires 1102 and 1104 of an electronically operated SERS-active system in accordance with embodiments of the present invention to produce a Raman spectrum. The nanowires 1102 and 1104 are each configured with a single QW 1106 and 1108, respectively, as described above with reference to FIG. 9A. As shown in FIG. 11, an analyte 1110 is introduced and the nanowires 1102 and 1104 are electronically pumped by a voltage source 1112 that causes the emission of Raman excitation light with Raman excitation wavelengths from the layers 1106 and 1108. As described above with reference to FIGS. 9A and 10, the light is substantially confined within, and emitted near the tip of, the nanowires 1102 and 1104. The Raman excitation wavelengths cause analytes 1110 located near the tips of the nanowires to produce a Raman spectrum of Raman scattered light over a range of emission wavelengths $\lambda_{em}$. The intensity of the Raman scattered light may also be enhanced as a result of surface plasmon polaritons formed on the nanoparticles, or charge transfer, as described above with reference to FIG. 4, producing an enhanced Raman spectrum, such as the Raman spectrum shown in FIG. 5.

III. Analyte Sensors and Detectors

Figure 12A:
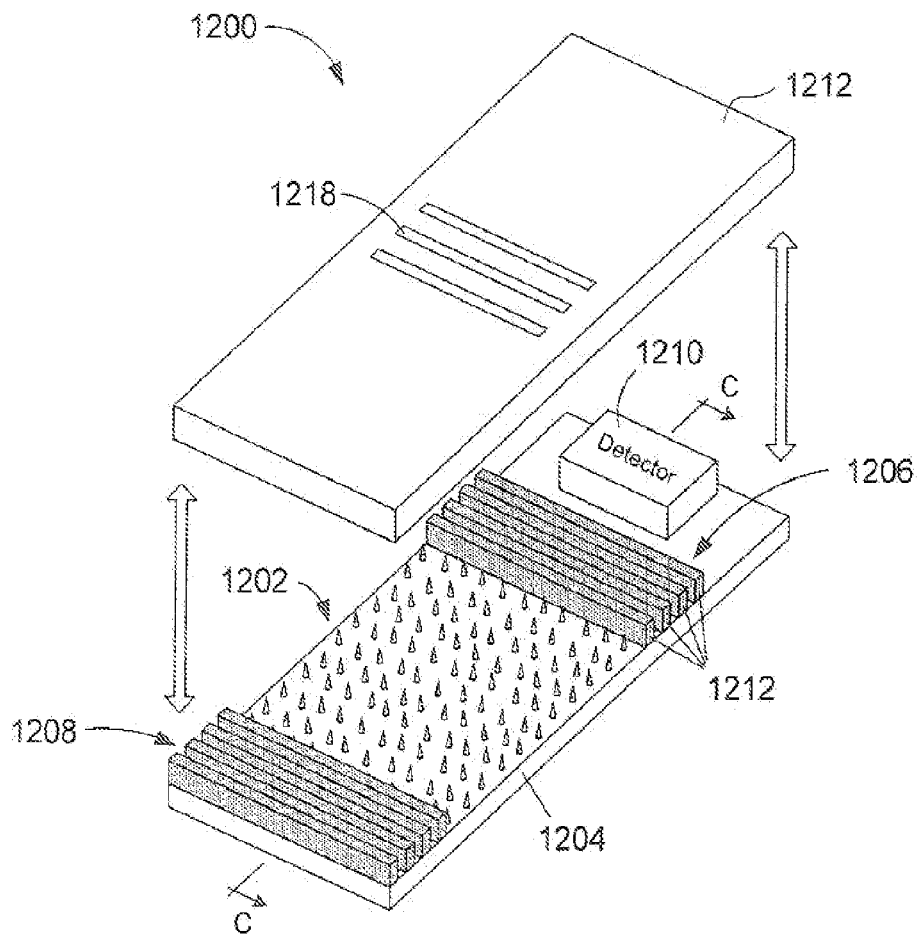
FIG. 12A shows an exploded isometric view and schematic representation of an exemplary analyte sensor configured in accordance with embodiments of the present invention.

FIG. 12A shows an exploded isometric view and schematic representation of an exemplary analyte sensor 1200 configured in accordance with embodiments of the present invention. The sensor 1200 includes a SERS-active system 1202 embedded in a substrate 1204. As shown in FIG. 12A, the SERS-active system 1202 is located between a first reflector 1206 and a second reflector 1208. The sensor 1200 also includes a detector 1210 disposed on the substrate 1204 and a cover 1212. The SERS-active system 1202 can be an optically or electronically pumped system, such as the systems 100 and 600 described above with reference to FIGS. 1 and 6, respectively.

Figure 12B:
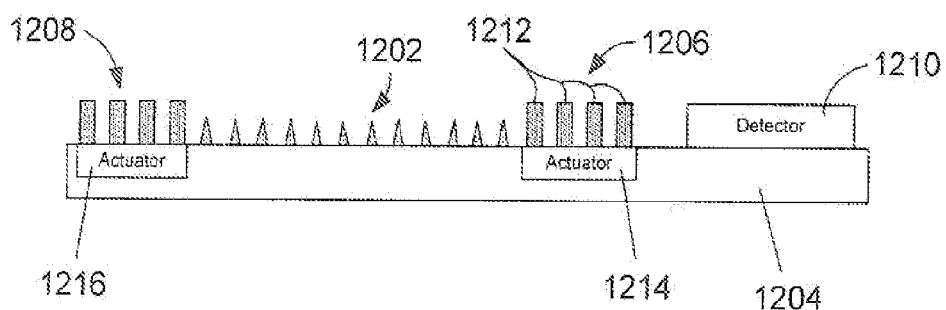
FIG. 12B shows a cross-sectional view of the sensor along a line C-C, shown in FIG. 12A, configured in accordance with embodiments of the present invention.

FIG. 12B shows a cross-sectional view of the substrate 1204 portion of the sensor 1200 along a line C-C, shown in FIG. 12A, in accordance with embodiments of the present invention. As shown in FIG. 12B, the reflectors 1206 and 1208 are each composed of thin layers of dielectric material separated by air, such as thin layers 1212. Appropriate selections of thin layer material, layer thickness, and layer spacing enable the reflectors 1206 and 1208 to be operated with a specified reflectivity for different wavelengths of light. FIG. 12B also reveals that the reflectors 1206 and 1208 are mechanically coupled to actuators 1214 and 1216, respectively. The actuators 1214 and 1216 can be separately operated to selectively adjust and tune the reflectivity of the reflectors 1206 and 1208 by controlling the separation distance between the thin layers. The separation distance can be controlled to produce ultra-high reflectivity minors of 99% or better over a narrow range of wavelengths, or the reflectors 1206 and 1208 can be tuned to reflect a broad spectrum of light.

The sensor 1200 is operated by introducing an analyte to the nanowires of the SERS-active system 1202. This can be accomplished by allowing an analyte in the gas phase to pass through ventilation holes 1218 formed in the cover 1212, as shown in FIG. 12A. In other embodiments, the analyte can be injected into the region between the SERS-active system 1202 and the cover 1212. In certain embodiments, when the SERS-active system 1202 is configured to be operated as an optically pumped SERS-active system 100, the nanowires are illuminated by light with an appropriate pump wavelength, as described above with reference to FIG. 4. In other embodiments, when the SERS-active system 1202 is configured to be operated as an electronically pumped SERS-active system 600, an appropriate forward bias is applied to the nanowires, as described above with reference to FIG. 11. The reflector 1208 can be tuned to operate as a nearly fully reflective minor for the wavelengths of light emitted from the analyte, and the reflector 1206 can be tuned to operate a partially reflective minor for the same wavelengths. As a result, the light emitted from the analyte resonates between the reflector 1206 and 1208, builds-up, and a portion the light eventually passes through the reflector 1206 and is detected by the detector 1210.

Figure 13:
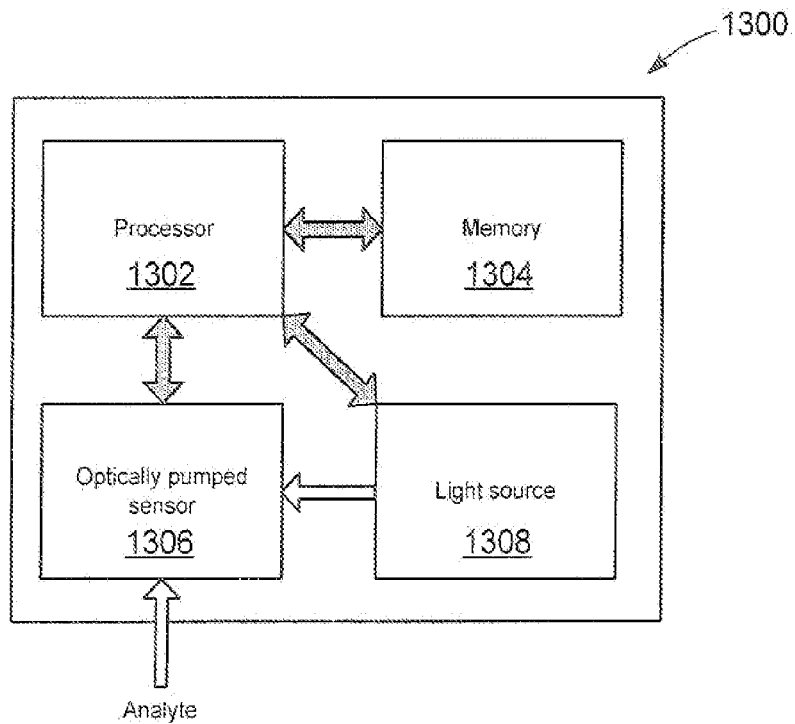
FIG. 13 shows a schematic representation of a first analyte detector configured in accordance with embodiments of the present invention.

The sensor 1200 can be implemented as a component of an application specific integrated circuit ("ASIC") configured to operate as an analyte detector. FIG. 13 shows a schematic representation of a first analyte detector ASIC 1300 configured in accordance with embodiments of the present invention. The detector 1300 includes a processor 1302, memory 1304, an optically pumped sensor 1306, and a light source 1308. The processor 1302 is in electronic communication with the memory 1304, the sensor 1306, and the light source 1308. The sensor 1306 can be configured as described above with reference to FIG. 12, but with an optically pumped SERA-active system 100. The memory 1304 can be flash memory that stores computer readable instructions for operating the light source 1308 and stores the information retrieved from the sensor 1306. The light source 1308 is configured to emit light directed toward to the sensor 1306 with wavelengths that pump the nanowires of the sensor 1306 as described above with reference to FIG. 4. The processor 1302 operates the reflectors of the sensor 1306 as described above with reference to FIG. 12, receives the Raman spectra results, and can store the results in memory 1304.

Figure 14:
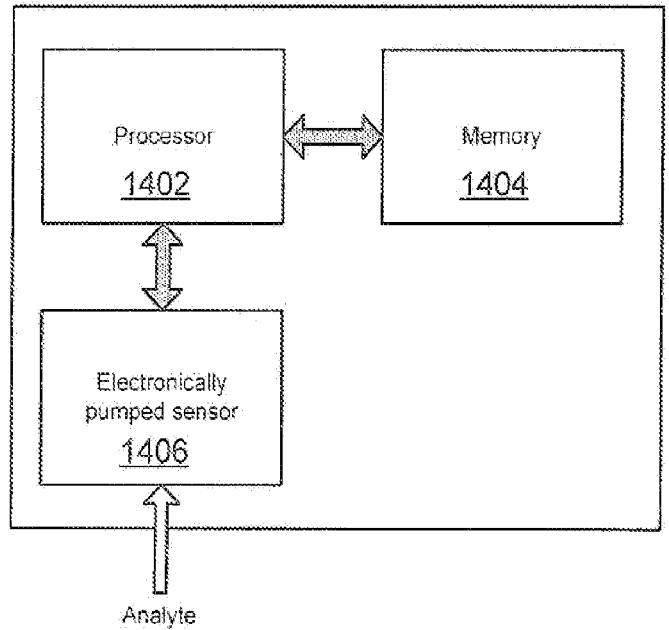
FIG. 14 shows a schematic representation of a second analyte detector configured in accordance with embodiments of the present invention.

FIG. 14 shows a schematic representation of a second analyte detector ASIC 1400 configured in accordance with embodiments of the present invention. The detector 1400 includes a processor 1402, memory 1404, and an electronically pumped sensor 1406. The processor 1402 is in electronic communication with the memory 1404 and the sensor 1406. The sensor 1406 can be configured as described above with reference to FIG. 12, but with an electronically operated SERS-active system 600. The memory 1404 can be flash memory that stores computer readable instructions for electronically operating the sensor 1406, as described above with reference to FIG. 12, and stores the information retrieved from the sensor 1406. The processor 1302 applies the appropriate voltage to the SERS-active system 1202, operates the reflectors of the sensor 1406 as described above with reference to FIG. 12, receives the Raman spectra results, and stores the results in memory 1404.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purposes of illustration and description. They are not intended to be exhaustive of or to limit the invention to the precise forms disclosed. Obviously, many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:
1. An analyte sensor, comprising:
 a system for performing surface-enhanced Raman spectroscopy, the system including:
  a substrate having a surface;
  a plurality of tapered nanowires disposed on the surface, each nanowire having a tapered end directed away from the surface; and
  a plurality of nanoparticles disposed on each nanowire, wherein when each nanowire is illuminated with light of a pump wavelength, Raman excitation light is emitted from the tapered end of the nanowire to interact with the nanoparticles and produce enhanced Raman scattered light from an analyte located in close proximity to the nanoparticles;

a first reflector disposed adjacent to the system and configured to partially reflect the Raman scattered light emitted from the analyte introduced to the system;

a second reflector disposed adjacent to the system opposite the first reflector and configured to reflect the Raman scattered light; and a photodetector positioned to detect the Raman scattered light transmitted through the first reflector, wherein the Raman scattered light corresponds to a Raman spectrum associated with the analyte.

2. The sensor of claim 1 wherein the nanowires further comprise one or more light emitters that emit Raman excitation light when illuminated with light of the pump wavelength.

3. The sensor of claim 2 wherein the light emitter further comprises at least one of: a quantum well, a quantum dot, an atom, and a molecule that emit the Raman excitation light when illuminated with light of the pump wavelength.

4. The sensor of claim 1 wherein the nanowires are configured so that the Raman excitation light is reflected toward the tapered end of the nanowires.

5. The sensor of claim 1 wherein the nanowires further comprise a semiconductor.

6. The sensor of claim 1 wherein the nanoparticles further comprises at least one of gold, silver, copper, or another suitable metal conductor.

7. The analyte sensor of claim 1, further comprising a first actuator mechanically coupled to the first reflector and a second actuator mechanically coupled to the second reflector, wherein the first actuator can be used to control the reflectivity of the first reflector, and the second actuator can be used to control the reflectivity of the second reflector.

8. An analyte sensor, comprising:
a system for performing surface-enhanced Raman spectroscopy, the system including:
  a first electrode layer disposed on a substrate;
  a dielectric layer disposed on the first electrode layer;
  a second electrode layer disposed on the dielectric layer; and
  a plurality of tapered nanowires disposed on the first electrode layer and extending through the dielectric layer and the second electrode layer, wherein applying an appropriate voltage to the first and second electrode layer causes each nanowire to emit Raman excitation light from the tapered end of the nanowire to interact with the nanoparticles and produce enhanced Raman scattered light from an analyte located in close proximity to the nanoparticles;

a first reflector disposed adjacent to the system and configured to partially reflect the Raman scattered light emitted from the analyte introduced to the system;

a second reflector disposed adjacent to the system opposite the first reflector and configured to reflect the Raman scattered light; and a photodetector positioned to detect the Raman scattered light transmitted through the first reflector, wherein the Raman scattered light corresponds to a Raman spectrum associated with the analyte.

9. The sensor of claim 8, further comprising a plurality of nanoparticles disposed near the tapered end of each nanowire, the nanoparticles composed of at least one of gold, silver, copper, or another suitable metal conductor to produce the enhanced Raman scattered light.

10. The sensor of claim 8, further comprising a portion of the second electrode layer covering at least a portion of the tapered end of each nanowire.

11. The sensor of claim 10 wherein the nanowires further comprise one or more light emitters embedded in the intrinsic semiconductor layer that emit the Raman excitation light when illuminated with light of the pump wavelength.

12. The sensor of claim 8 wherein the nanowires further comprise an n-type semiconductor layer and a p-type semiconductor layer that emit the Raman excitation light when illuminated with light of the pump wavelength.

13. The sensor of claim 8 wherein the nanowires further comprise an intrinsic semiconductor layer sandwiched between an n-type semiconductor layer and a p-type semiconductor layer that emit the Raman excitation light when illuminated with light of the pump wavelength.

14. The sensor of claim 8 wherein the first electrode layer and the second electrode each further comprise gold, silver, copper, or another suitable metal conductor.

* * * * *